United States Patent [19]

Flanigen et al.

[11] Patent Number: 4,913,888
[45] Date of Patent: * Apr. 3, 1990

[54] ARSENIC-ALUMINUM-PHOSPHORUS-OXIDE MOLECULAR SIEVE COMPOSITIONS

[75] Inventors: Edith M. Flanigen, White Plains; Brent M. T. Lok, New City; Robert L. Patton, Katonah; Stephen T. Wilson, Shrub Oak, all of N.Y.

[73] Assignee: UOP, Des Plaines, Ill.

[*] Notice: The portion of the term of this patent subsequent to Aug. 11, 2004 has been disclaimed.

[21] Appl. No.: 830,889

[22] Filed: Feb. 19, 1986

Related U.S. Application Data

[63] Continuation-in-part of Ser. No. 600,166, Apr. 13, 1984, abandoned.

[51] Int. Cl.$^4$ ............................................. C01B 25/36
[52] U.S. Cl. ..................................... 423/306; 423/601
[58] Field of Search ............... 423/305, 306, 601, 602; 502/208, 214

[56] References Cited

U.S. PATENT DOCUMENTS

| | | | |
|---|---|---|---|
| 3,941,871 | 3/1976 | Dwyer et al. | 423/326 |
| 3,981,970 | 9/1976 | Wada et al. | 423/306 |
| 4,061,724 | 12/1977 | Grose et al. | 423/335 |
| 4,310,440 | 1/1982 | Wilson et al. | 423/305 |
| 4,420,467 | 12/1983 | Whittam | 423/328 |
| 4,440,871 | 4/1984 | Lok et al. | 208/114 |
| 4,456,582 | 6/1984 | Marosi et al. | 423/326 |
| 4,500,651 | 2/1985 | Lok et al. | 502/208 |
| 4,554,143 | 11/1985 | Messina et al. | 423/306 |
| 4,567,029 | 1/1986 | Wilson et al. | 502/208 |

FOREIGN PATENT DOCUMENTS

| | | |
|---|---|---|
| 0054364 | 6/1982 | European Pat. Off. . |
| 0055046 | 6/1982 | European Pat. Off. . |
| 0055529 | 7/1982 | European Pat. Off. . |
| 0059059 | 9/1982 | European Pat. Off. . |
| 0147991 | 7/1985 | European Pat. Off. ............ 423/306 |
| 02078704 | 1/1982 | United Kingdom . |

OTHER PUBLICATIONS

Haggin, "Chemical & Engineering", Jun. 20, 1986, pp. 36 & 37.

*Primary Examiner*—John Doll
*Assistant Examiner*—R. Bruce Breneman
*Attorney, Agent, or Firm*—Thomas K. McBride; Eugene I. Snyder; Frank S. Molinaro

[57] ABSTRACT

Molecular sieve compositions having three-dimensional microporous framework structures of $AsO_2$, $AlO_2$ and $PO_2$ tetrahedral oxide units are disclosed. These molecular sieves have an empirical chemical composition on an anhydrous basis expressed by the formula:

mR: $(As_xAl_yP_z)O_2$ 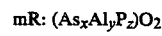

wherein "R" represents at least one organic templating agent present in the intracrystalline pore system; "m" represents the molar amount of "R" present per mole of $(As_xAl_yP_z)O_2$; and "x", "y" and "z" represent the mole fractions of arsenic, aluminum and phosphorus, respectively, present as tetrahedral oxides. Their use as adsorbents, catalysts, etc. is also disclosed.

13 Claims, 3 Drawing Sheets

ARSENIC-ALUMINUM-PHOSPHORUS-OXIDE MOLECULAR SIEVE COMPOSITIONS

This application is a continuation-in-part of our co-pending application Ser. No. 600,166 filed Apr. 13, 1984, now abandoned.

FIELD OF THE INVENTION

The instant invention relates to a novel class of crystalline microporous molecular sieves and to the method of their preparation. The invention relates to novel arsenic-aluminum-phosphorus-oxide molecular sieves containing framework tetrahedral oxide units of arsenic, aluminum and phosphorus. These compositions may be prepared hydrothermally from gels containing reactive compounds of arsenic, aluminum and phosphorus capable of forming framework tetrahedral oxides, and preferably at least one organic templating agent which functions in part to determine the course of the crystallization mechanism and the structure of the crystalline product.

BACKGROUND OF THE INVENTION

Molecular sieves of the crystalline aluminosilicate zeolite type are well known in the art and now comprise over 150 species of both naturally occurring and synthetic compositions. In general the crystalline zeolites are formed from corner-sharing $AlO_2$ and $SiO_2$ tetrahedra and are characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain $AlO_2$ tetrahedra as essential framework constituents, but which exhibit the ion-exchange and/or adsorption characteristics of the zeolites are also known. Metal organosilicates which are said to possess ion-exchange properties, have uniform pores and are capable of reversibly adsorbing molecules having molecular diameters of about 6 Å or less, are reported in U.S. Pat. No. 3,941,871 issued Mar. 2, 1976 to Dwyer et al. A pure silica polymorph, silicalite, having molecular sieving properties and a neutral framework containing neither cations nor cation sites is disclosed in U.S. Pat. No. 4,061,724 issued Dec. 6, 1977 to R. W. Grose et al.

A recently reported class of microporous compositions and the first framework oxide molecular sieves synthesized without silica, are the crystalline galuminophosphate compositions disclosed in U.S. Pat. No. 4,310,440 issued Jan. 12, 1982 to Wilson et al. These materials are formed from $AlO_2$ and $PO_2$ tetrahedra and have electrovalently neutral frameworks as in the case of silica polymorphs. Unlike the silica molecular sieve, silicalite, which is hydrophobic due to the absence of extra-structural cations, the aluminophosphate molecular sieves are moderately hydrophilic, apparently due to the difference in electro-negativity between aluminum and phosphorus. Their intracrystalline pore volumes and pore diameters are comparable to those known for zeolites and silica molecular sieves.

In U.S. Pat. No. 4,440,871 there is described a novel class of silicon-substituted aluminophosphates which are both microporous and crystalline. The materials have a three dimensional crystal framework of $PO_2^+$, $AlO_2^-$ and $SiO_2$ tetrahedral units and, exclusive of any alkali metal or calcium which may optionally be present, an as-synthesized empirical chemical composition on an anhydrous basis of:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular silicoaluminophosphate species involved; and "x", "y", and "z" represent the mole fractions of silicon, aluminum and phosphorus, respectively, present as tetrahedral oxides. The minimum value for each of "x", "y", and "z" is 0.01 and preferably 0.02. The maximum value for "x" is 0.98; for "y" is 0.60; and for "z" is 0.52. These silicoaluminophosphates exhibit several physical and chemical properties which are characteristic of aluminosilicate zeolites and aluminophosphates.

In U.S. Pat. No. 4,500,651, there is described a novel class of titanium-containing molecular sieves whose chemical composition in the as-synthesized and anhydrous form is represented by the unit empirical formula:

$$mR:(Ti_xAl_yP_z)O_2$$

wherein "R" represents at least one organic templating agent present in the intracrystalline pore system; "m" represents the moles of "R" present per mole of $(Ti_xAl_yP_z)O_2$ and has a value of between zero and about 5.0; and "x", "y" and "z" represent the mole fractions of titanium, aluminum and phosphorus, respectively, present as tetrahedral oxides.

In U.S. Pat. No. 4,567,029, there is described a novel class of crystalline metal aluminophosphates having three-dimensional microporous framework structures of $MO_2$, $AlO_2$ and $PO_2$ tetrahedral units and having an empirical chemical composition on an anhydrous basis expressed by the formula:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3; "M" represents at least one metal of the group magnesium, manganese, zinc and cobalt; "x", "y", and "z" represent the mole fractions of the metal "M", aluminum and phosphorus, respectively, present as tetrahedral oxides.

In U.S. Pat. No. 4,544,143, there is described a novel class of crystalline ferro-aluminophosphates having a three-dimensional microporous framework structure of $FeO_2$, $AlO_2$ and $PO_2$ tetrahedral units and having an empirical chemical composition on an anhydrous basis expressed by the formula:

$$mR:(Fe_xAl_yP_z)O_2$$

wherein "R" represents at least one organic templating agent present in the intracrystalline pore system; "m" represents the moles of "R" present per mole of $(Fe_xAl_yP_z)O_2$ and has a value of from zero to 0.3; and "x", "y" and "z" represent the mole fractions of the iron, aluminum and phosphorus, respectively, present as tetrahedral oxides.

The instant invention relates to new molecular sieve compositions having framework tetrahedral units of $AsO_2^n$, $AlO_2^-$ and $PO_2^+$ where "n" is $-1$ or $+1$.

DESCRIPTION OF THE FIGURES

FIG. 4 is a ternary diagram wherein parameters relating to the reaction mixtures employed in the preparation of the compositions of this invention are set forth as mole fractions.

SUMMARY OF THE INVENTION

The instant invention relates to a new class of arsenic-aluminum-phosphorus-oxide molecular sieves having a crystal framework structure of $AsO_2^n$, $AlO_2^-$ and $PO_2^+$ tetrahedral oxide units where "n" is $-1$ or $+1$. These new molecular sieves exhibit ion-exchange, adsorption and catalytic properties and, accordingly, find wide use as adsorbents and catalysts. The members of this novel class of compositions have crystal framework structures of $ASO_2^n$, $AlO_2^-$ and $PO_2^+$ tetrahedran units and have an empirical chemical composition on an anhydrous basis expressed by the formula:

wherein "R" represents at least one organic templating agent present in the intracrystalline pore system; "m" represents the molar amount of "R" present per mole of $(As_xAl_yP_z)O_2$ and has a value of zero to about 0.3; and "x", "y" and "z" represent the mole fractions of arsenic, aluminum and phosphorus, respectively, present as tetrahedral oxides. These molecular sieve compositions comprise crystalline molecular sieves having a three-dimensional microporous framework structure of $AsO_2^n$, $AlO_2^-$ and $PO_2^+$ tetrahedral units where "n" is $-1$ or $+1$.

The molecular sieves of the instant invention will be generally referred to by the acronym "AsAPO" to designate the framework of $AsO_2^n$, $AlO_2^-$ and $PO_2^+$ tetrahedral units. Actual class members will be identified by denominating the various structural species which make up the AsAPO class by assigning a number and, accordingly, are identified as "AsAPO-i" wherein "i" is an integer. The given species designation is not intended to denote a similarity in structure to any other species denominated by a numbering system.

DETAILED DESCRIPTION OF THE INVENTION

The instant invention relates to a new class of arsenic-aluminum-phosphorus-oxide molecular sieves comprising a crystal framework structure of $AsO_2^n$, $AlO_2^-$ and $PO_2^+$ tetrahedral oxide units. These new molecular sieves exhibit ion-exchange, adsorption and catalytic properties and, accordingly, find wide use as adsorbents and catalysts.

Figure 1:
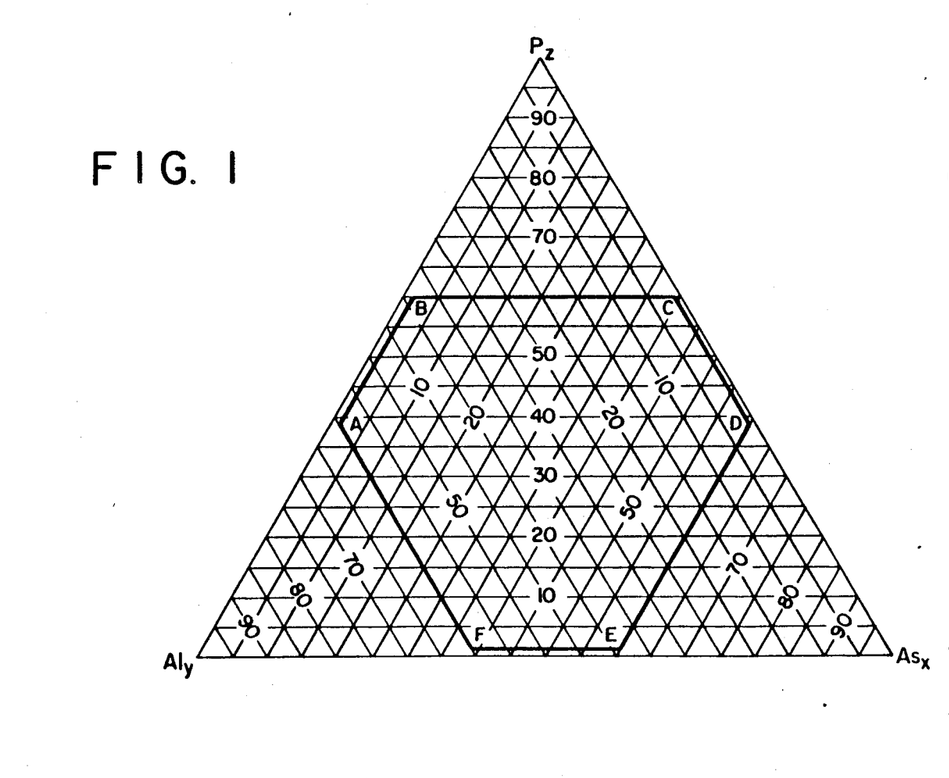
FIG. 1 is a ternary diagram wherein parameters relating to the instant compositions are set forth as mole fractions.

The AsAPO molecular sieves have three-dimensional microporous framework structures of $AsO_2^n$, $AlO_2^-$, and $PO_2^+$ tetrahedral oxide units, where "n" is $-1$ or $+1$, having an empirical chemical composition on a n anhydrous basis expressed by the formula:

wherein "R" represents at least one organic templating agent present in the intracrystalline pore system; "m" represents the molar amount of "R" present per mole of $(As_xAl_yP_z)O_2$ and has a value of zero to about 0.3 but is preferably not greater than about 0.15; and "x", "y" and "z" represent the mole fractions of arsenic, aluminum and phosphorus, respectively, present as tetrahedral oxides. The mole fractions "x", "y", and "z" are generally defined as being within the hexagonal compositional area defined by points A, B, C, D, E and F of the ternary diagram of FIG. 1. Points A, B, C, D, E and F of FIG. 1 have the following values for "x", "y", and "z":

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01 |

Figure 2:
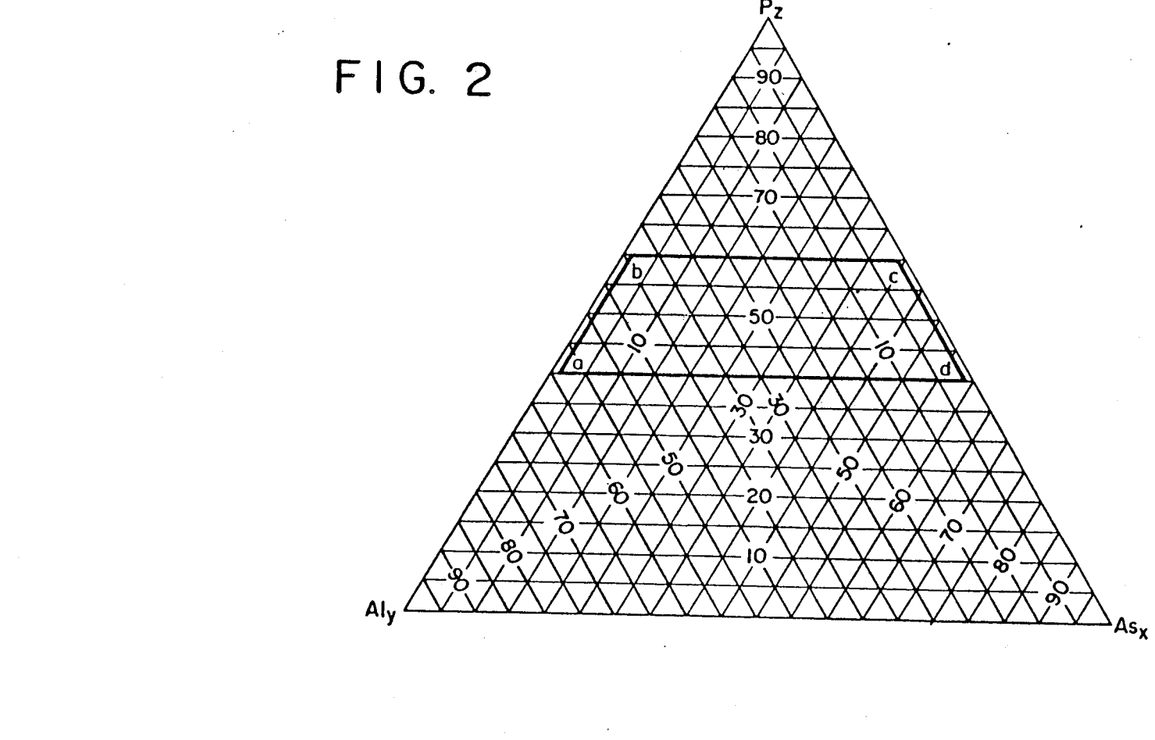
FIG. 2 is a ternary diagram wherein parameters relating to preferred compositions are set forth as mole fractions.
Figure 3:
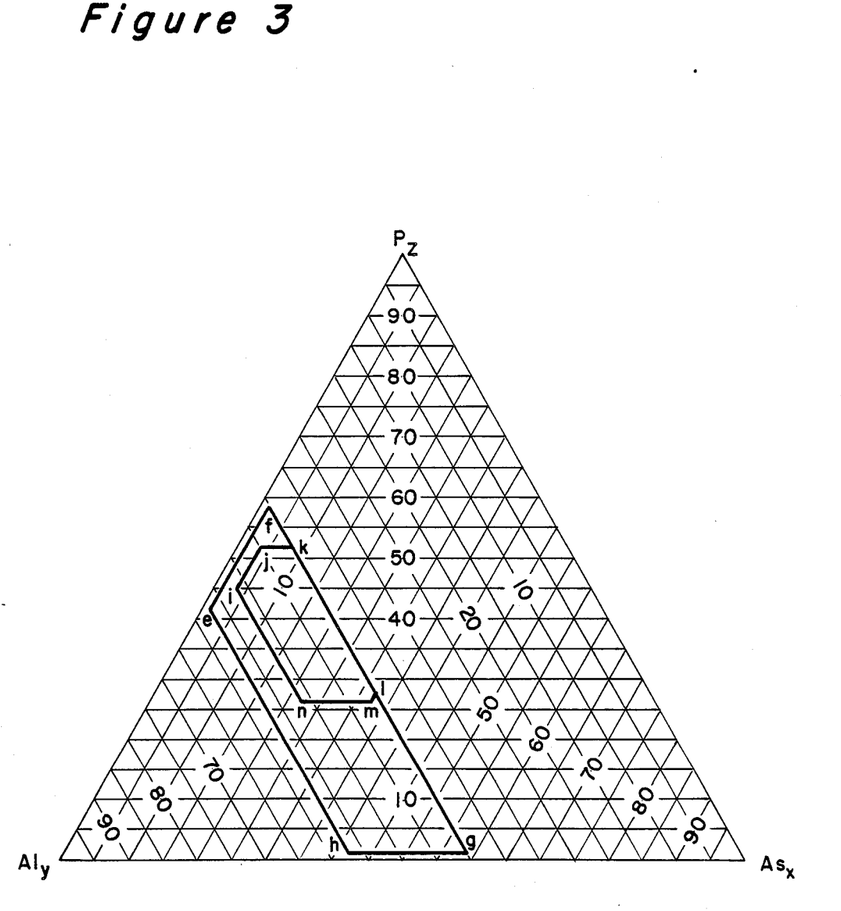
FIG. 3 is a ternary diagram wherein parameters relating to preferred compositions are set forth as mole fractions.

There are two preferred subclasses of the AsAPO molecular sieves since the value of "n" in $AsO_2^n$ can be either $-1$ or $+1$. Accordingly, the values of "x", "y" and "z" in the above formula are defined by reference to the value of "n" it being understood that mixtures of such are permitted in a given AsAPO. The values of "x", "y" and "z" for "n" $= -1$ are within the tetragonal compositional area defined by the points a, b, c and d of the ternary diagram which is FIG. 2 of the drawings and the values of "x", "y" and "z" for "n" $= +1$ are within the tetragonal compositional area defined by the points e, f, g and h of the ternary diagram which is FIG. 3 of the drawings, said points a, b, c and d representing the following values for "x", "y" and "z":

| Point | Mole Fraction | | |
|---|---|---|---|
| | x | y | z |
| a | 0.01 | 0.59 | 0.40 |
| b | 0.01 | 0.39 | 0.60 |
| c | 0.39 | 0.01 | 0.60 |
| d | 0.59 | 0.01 | 0.40 | said points e, f, g and h representing the following values for "x", "y" and "z":

| Point | Mole Fraction | | |
|---|---|---|---|
| | x | y | z |
| e | 0.01 | 0.60 | 0.39 |
| f | 0.01 | 0.40 | 0.59 |
| g | 0.59 | 0.40 | 0.01 |
| h | 0.39 | 0.60 | 0.01 |

In an especially preferred subclass of the AsAPO molecular sieves in which "n" $= +1$, the values of "x", "y" and "z" in the formula are within the hexagonal compositional area defined by the points i, j, k, l, m, and n of the ternary diagram which is FIG. 3 of the drawings, said points i, j, k, l, m, and n representing the following values for "x", "y" and "z":

| Point | Mole Fraction | | |
|---|---|---|---|
| | x | y | z |
| i | 0.03 | 0.52 | 0.45 |
| j | 0.03 | 0.45 | 0.52 |
| k | 0.08 | 0.40 | 0.52 |
| l | 0.33 | 0.40 | 0.27 |
| m | 0.33 | 0.41 | 0.26 |
| n | 0.22 | 0.52 | 0.26 |

The AsAPO compositions preferably contain not more than about 0.6 moles of water per mole of $(As_xAl_yP_z)O_2$.

The AsAPOs of this invention are useful as adsorbents, catalysts, ion-exchangers, and the like in much the same fashion as aluminosilicates have been employed heretofore, although their chemical and physical properties are not necessarily similar to those observed for aluminosilicates.

AsAPO compositions are generally synthesized by hydrothermal crystallization from a reaction mixture containing reactive sources of arsenic, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure, at a temperature between 50° and 250° C., and preferably between 100° C. and 200° C. until crystals of the AsAPO product are obtained, usually a period of from several hours to several weeks. Typical crystallization times are from about 2 hours to about 30 days with from about 2 hours to about 20 days, and preferably about 12 hours to about 7 days, being generally employed to obtain crystals of the AsAPO products. The product is recovered by any convenient method such as centrifugation or filtration.

In synthesizing the AsAPO compositions of the instant invention, it is preferred to employ a reaction mixture composition expressed in terms of the molar ratios as follows:

$$aR\ (As_uAl_vP_w)O_2: bH_2O$$

wherein "R" is an organic templating agent; "a" is the amount of organic templating agent "R" and has a value of from zero to about 6 and is preferably an effective amount within the range of greater than zero (0) to about 6 and most preferably not more than about 0.5; "b" has a value of from zero (0) to about 500, preferably between about 2 and about 300, most preferably not greater than about 20; and --u--,--v-- and --w-- represent the mole fractions of arsenic, aluminum and phosphorus, respectively, and each has a value of at least 0.01. The mole fractions --u--,--v-- and --w-- in the reaction mixture are preferably within the pentagonal compositional area defined by points G, H, I, J and K which is shown in FIG. 4 of the drawings, where points G, H, I, J and K have the following values for --u--,--v-- and --w-- and "z":

| Point | Mole Fraction | | |
|---|---|---|---|
| | u | v | w |
| G | 0.01 | 0.60 | 0.39 |
| H | 0.01 | 0.39 | 0.60 |
| I | 0.39 | 0.01 | 0.60 |
| J | 0.98 | 0.01 | 0.01 |
| K | 0.39 | 0.60 | 0.01 |

Especially preferred reaction mixture compositions are those within the hexagonal compositional area defined by points a, b, c, d, e and f which is shown in FIG. 4 of the drawings, where points a, b, c, d, e and f have the following values for "x", "y" and "z":

| Point | Mole Fraction | | |
|---|---|---|---|
| | u | v | w |
| a | 0.20 | 0.55 | 0.25 |
| b | 0.20 | 0.50 | 0.30 |
| c | 0.30 | 0.40 | 0.30 |
| d | 0.40 | 0.40 | 0.20 |
| e | 0.40 | 0.50 | 0.10 |
| f | 0.35 | 0.55 | 0.10 |

In the foregoing expression of the reaction composition, the reactants are normalized with respect to the total of $x+y+z=1.00$ mole, whereas in the examples the reaction mixtures are expressed in terms of the molar oxide ratios and may be normalized to 1.00 mole of $P_2O_5$. This latter form is readily converted to the former form by routine calculation by dividing the total number of moles of arsenic, aluminum and phosphorus into the moles of each of the aforementioned elements arsenic, aluminum and phosphorus. The moles of template and water are similarly normalized by dividing by the total moles of arsenic, phosphorus and aluminum.

In forming the reaction mixture from which the instant molecular sieves are formed the organic templating agent can be any of those heretofore proposed for use in the synthesis of conventional zeolite aluminosilicates. In general these compounds contain elements of Group VA of the Periodic Table of Elements, particularly nitrogen, phosphorus, arsenic and antimony, preferably nitrogen or phosphorus and most preferably nitrogen, which compounds also contain at least one alkyl or aryl group having from 1 to 8 carbon atoms. Particularly preferred compounds for use as templating agents are the amines, quaternary phosphonium and quaternary ammonium compounds, the latter being represented generally by the formula $R_4X^+$ wherein "X" is nitrogen or phosphorus and each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. The mono-, di- and tri-amines are advantageously utilized, either alone or in combination with a quaternary ammonium compound or other templating compound. Mixtures of two or more templating agents can either produce mixtures of the desired AsAPOs or the more strongly directing templating species may control the course of the reaction with the other templating species serving primarily to establish the pH conditions of the reaction el. Representative templating agents include tetramethylammonium, tetraethylammonium, tetrapropylammonium or tetrabutylammonium ions; tetrapentylammonium ion; di-n-propylamine; tripropylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo (2,2,2,) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. Not every templating agent will direct the formation of every species of AsAPO, i.e., a single templating agent can, with proper manipulation of the reaction condition, direct the formation of several AsAPO compositions, and a given AsAPO composition can be produced using several different templating agents.

The reactive phosphorus source is preferably phosphoric acid, but organic phosphates such as triethyl phosphate may be satisfactory, and so also may crystalline or amorphous aluminophosphates such as the AlPO$_4$ composition of U.S. Pat. No. 4,310,440. Organophosphorus compounds, such as tetrabutylphosphonium bromide, do not apparently serve as reactive sources of phosphorus, but these compounds may function as templating agents. Conventional phosphorus salts such as sodium metaphosphate, may be used, at least in part, as the phosphorus source, but are not preferred.

The preferred aluminum source is either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The reactive source of arsenic can be introduced into the reaction system in any form which permits the formation in situ of a reactive form of arsenic, i.e., reactive to form the framework tetrahedral oxide unit of arsenic. Compounds of arsenic which may be employed include oxides, alkoxides, hydroxides, chlorides, bromides, iodides, nitrates, sulfates, carboxylates (e.g., acetates) and the like.

While not essential to the synthesis of AsAPO compositions, stirring or other moderate agitation of the reaction mixture and/or seeding the reaction mixture with seed crystals of either the AsAPO species to be produced or a topologically similar aluminophosphate, aluminosilicate or molecular sieve composition, facilitates the crystallization procedure.

After crystallization the AsAPO product may be isolated and advantageously washed with water and dried in air. The as-synthesized AsAPO generally contains within its internal pore system at least one form of the templating agent employed in its formation. Most commonly the organic moiety is present, at least in part, as a charge-balancing cation as is generally the case with as-synthesized aluminosilicate zeolites prepared from organic-containing reaction systems. It is possible, however, that some or all of the organic moiety is an occluded molecular species in a particular AsAPO species. As a general rule the templating agent, and hence the occluded organic species, is too large to move freely through the pore system of the AsAPO product and must be removed by calcining the AsAPO at temperatures of 200° C. to 700° C., preferably about 350° C. to about 600° C., to thermally degrade the organic species. In a few instances the pores of the AsAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein does not include the condition of the AsAPO phase wherein the organic moiety occupying the intracrystalline pore system as a result of the hydrothermal crystalline process has been reduced by post-synthesis treatment such that the value of "m" in the composition formula $$mR (As_xAl_yP_z)O_2$$

has a value of less than 0.02. The other symbols of the formula are as defined hereinabove. In those preparations in which an alkoxide is employed as the source of arsenic, aluminum or phosphorus, the corresponding alcohol is necessarily present in the reaction mixture since it is a hydrolysis product of the alkoxide It has not been determined whether this alcohol participates in the synthesis process as a templating agent. For the purposes of this application, however, this alcohol is arbitrarily omitted from the class of templating agents, even if it is present in the assynthesized AsAPO material.

Since the present AsAPO compositions are formed from AsO$_2^n$, AlO$_2$, PO$_2$, tetrahedral units which, respectively, have a net charge of "n" (−1 or +1), −1 and +1, the matter of cation exchangeability is considerably more complicated than in the case of zeolitic molecular sieves in which, ideally, there is a stoichiometric relationship between AlO$_2^-$ tetrahedra and charge-balancing cations. In the instant compositions, an AlO$_2^-$ tetrahedron can be balanced electrically either by association with a PO$_2^+$ tetrahedron or a simple cation such as an alkali metal cation, a proton (H$^+$), a cation of arsenic present in the reaction mixture, or an organic cation derived from the templating agent. Similarly, an AsO$_2^-$ tetrahedron can be balanced electrically by association with PO$_2^+$ tetrahedra, a cation of arsenic present in the reaction mixture, a simple cation such as an alkali metal cation, a proton (H$^+$), organic cations derived from the templating agent, or other divalent or polyvalent metal cations introduced from an extraneous source. It has also been postulated that non-adjacent AlO$_2^-$ and PO$_2^+$ tetrahedral pairs can be balanced by Na$^+$ and OH$^-$ respectively [Flanigen and Grose, Molecular Sieve Zeolites-I, ACS, Washington, DC (1971)].

The AsAPO compositions of the present invention may exhibit cation-exchange capacity when analyzed using ion-exchange techniques heretofore employed with zeolitic aluminosilicates and have pore diameters which are inherent in the lattice structure of each species and which are at least about 3 Å in diameter. Ion exchange of AsAPO compositions is ordinarily possible only after any organic moiety derived from the template, present as a result of synthesis, has been removed from the pore system. Dehydration to remove water present in the assynthesized AsAPO compositions can usually be accomplished, to some degree at least, in the usual manner without removal of the organic moiety, but the absence of the organic species greatly facilitates adsorption and desorption procedures. The AsAPO materials have various degrees of hydrothermal and thermal stability, some being quite remarkable in this regard, and function well as molecular sieve adsorbents and hydrocarbon conversion catalysts or catalyst bases.

In preparing the AsAPO composition it is preferred to use a stainless steel reaction vessel lined with an inert plastic material, e.g., polytetrafluoroethylene, to avoid contamination of the reaction mixture. In general, the final reaction mixture from which each AsAPO composition is crystallized is prepared by forming mixtures of less than all of the reagents and thereafter incorporating into these mixtures additional reagents either singly or in the form of other intermediate mixtures of two or more reagents. In some instances the reagents admixed retain their identity in the intermediate mixture and in other cases some or all of the reagents are involved in chemical reactions to produce new reagents. The term "mixture" is applied in both cases. Further, it is preferred that the intermediate mixtures as well as the final reaction mixtures be stirred until substantially homogeneous.

X-ray patterns of reaction products are obtained by X-ray analysis using either: (1) two computer interfaced Seimen's D-500 X-ray powder diffractometers, available from Seimens Corporation, Cherry Hill, N.J., equipped with Seimens Type K-805 X-ray sources; or (2) standard X-ray powder diffraction techniques. When the standard technique is employed the radiation source is a high-intensity, copper target, X-ray tube operated at 50 Kv and 40 ma. The diffraction pattern from the copper K-alpha radiation and graphite monochromator is suitably recorded by an X-ray spectrometer scintillation counter, pulse height analyzer and strip chart recorder. X-ray patterns are obtained using flat compressed powder samples which are scanned at 2° (2 theta) per minute, using a two second time constant.

All interplanar spacings (d) in Angstrom units are obtained from the position of the diffraction peaks expressed as $2\theta$ where $\theta$ is the Bragg angle as observed on the strip chart. Intensities are determined from the heights of diffraction peaks after subtracting background, "$I_o$" being the intensity of the strongest line or peak, and "I" being the intensity of each of the other peaks.

As will be understood by those skilled in the art the determination of the parameter 2 theta is subject to both human and mechanical error, which in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m, w and vw which represent very strong, strong, medium, weak and very weak, respectively.

In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The molecular sieves of the instant invention may be characterized by their X-ray powder diffraction patterns and as such may have one of the X-ray patterns set forth in the following Tables A through V, wherein said X-ray patterns are for the as-synthesized form unless otherwise noted. In most cases, the pattern of the corresponding calcined form will also fall within the relevant Table. However, in some cases the removal of the occluded templating agent which occurs during calcination will be accompanied by sufficient relaxation of the lattice to shift some of the lines slightly outside the ranges specified in the relevant Table. In a small number of cases, calcination appears to cause more substantial distortions in the crystal lattice, and hence more significant changes in the X-ray powder diffraction pattern.

TABLE A (AsAPO-5)

| $2\theta$ | d(Å) | Relative Intensity |
|---|---|---|
| 7.3–7.65 | 12.1–11.56 | m–vs |
| 19.5–19.95 | 4.55–4.46 | m–s |
| 20.9–21.3 | 4.25–4.17 | m–vs |
| 22.2–22.6 | 4.00–3.93 | w–vs |
| 25.7–26.15 | 3.47–3.40 | w–m |

TABLE B (AsAPO-11)

| $2\theta$ | d(Å) | Relative Intensity |
|---|---|---|
| 9.3–9.65 | 9.51–9.17 | m–s |
| 20.2–20.6 | 4.40–4.31 | m–s |
| 20.9–21.3 | 4.25–4.17 | s–vs |
| 22.0–22.5 | 4.04–3.95 | m–s |
| 22.5–22.9 | 3.95–3.92 | m–s |
| 23.0–23.4 | 3.87–3.80 | m–vs |

TABLE C (AsAPO-14)

| $2\theta$ | d(Å) | Relative Intensity |
|---|---|---|
| 8.6–8.9 | 10.3–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE D (AsAPO-16)

| $2\theta$ | d(Å) | Relative Intensity |
|---|---|---|
| 11.3–11.6 | 7.83–7.63 | m–vs |
| 18.7–18.9 | 4.75–4.70 | w–s |
| 21.9–22.3 | 4.06–3.99 | m–vs |
| 26.5–27.0 | 3.363–3.302 | w–m |
| 29.7–30.05 | 3.008–2.974 | w–m |

TABLE E (AsAPO-17)

| $2\theta$ | d(Å) | Relative Intensity |
|---|---|---|
| 7.7–7.75 | 11.5–11.4 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

TABLE F (AsAPO-18)

| $2\theta$ | d(Å) | Relative Intensity |
|---|---|---|
| 9.5–9.65 | 9.27–9.16 | vs |
| 15.4–15.55 | 5.76–5.70 | m |
| 16.9–17.1 | 5.25–5.19 | m |

TABLE F-continued

| 2θ | (AsAPO-18) d(Å) | Relative Intensity |
|---|---|---|
| 20.0–20.25 | 4.44–4.39 | m |
| 20.8–21.05 | 4.27–4.22 | m |
| 31.8–32.5 | 2.814–2.755 | m |

TABLE G

| 2θ | (AsAPO-20) d(Å) | Relative Intensity |
|---|---|---|
| 13.7–14.25 | 6.46–6.22 | m–vs |
| 19.55–20.0 | 4.54–4.44 | w–s |
| 24.05–24.5 | 3.70–3.63 | m–vs |
| 34.3–35.0 | 2.614–2.564 | vw–w |
| 42.5–43.0 | 2.127–2.103 | vw–w |

TABLE H

| 2θ | (AsAPO-31) d(Å) | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

TABLE J*

| 2θ | (AsAPO-33) d(Å) | Relative Intensity |
|---|---|---|
| 9.25–9.55 | 9.56–9.26 | w–m |
| 12.5–12.9 | 7.08–6.86 | vs |
| 16.9–17.3 | 5.25–5.13 | w–m |
| 20.45–20.9 | 4.34–4.25 | w–m |
| 23.85–24.25 | 3.73–3.67 | w–m |
| 26.05–26.35 | 3.42–3.38 | w–m |
| 27.3–27.6 | 3.27–3.23 | vs |

*as-synthesized form

TABLE K*

| 2θ | (AsAPO-33) d(Å) | Relative Intensity |
|---|---|---|
| 13.15–13.4 | 6.73–6.61 | vs |
| 18.05–18.35 | 4.91–4.83 | m |
| 18.4–18.6 | 4.82–4.77 | m |
| 26.55–26.7 | 3.36–3.34 | m |
| 32.0–32.1 | 2.80–2.79 | m |

*calcined form

TABLE L

| 2θ | (AsAPO-34) d(Å) | Relative Intensity |
|---|---|---|
| 9.4–9.65 | 9.41–9.17 | s–vs |
| 15.9–16.2 | 5.57–5.47 | vw–m |
| 17.85–18.4 | 4.97–4.82 | w–s |
| 20.3–20.9 | 4.37–4.25 | m–vs |
| 24.95–25.4 | 3.57–3.51 | vw–s |
| 30.3–30.8 | 2.95–2.90 | w–s |

TABLE M

| 2θ | (AsAPO-35) d(Å) | Relative Intensity |
|---|---|---|
| 10.8–11.1 | 8.19–7.97 | m |
| 17.2–17.4 | 5.16–5.10 | s–vs |
| 21.0–21.25 | 4.23–4.18 | m–s |
| 21.8–22.0 | 4.08–4.04 | vs |
| 31.8–32.2 | 2.814–2.788 | m |

TABLE N

| 2θ | (AsAPO-36) d(Å) | Relative Intensity |
|---|---|---|
| 7.7–7.9 | 11.5–11.2 | vs |
| 16.2–16.6 | 5.47–5.34 | w–m |
| 18.9–19.3 | 4.70–4.60 | m–s |
| 20.6–20.8 | 4.31–4.27 | w–s |
| 21.8–22.0 | 4.08–4.04 | m |
| 22.2–22.5 | 4.00–3.95 | w–m |

TABLE O

| 2θ | (AsAPO-37) d(Å) | Relative Intensity |
|---|---|---|
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

TABLE P

| 2θ | (AsAPO-39) d(Å) | Relative Intensity |
|---|---|---|
| 9.4–9.6 | 9.41–9.21 | w–m |
| 13.3–13.6 | 6.66–6.51 | m–vs |
| 18.0–18.4 | 4.93–4.82 | m |
| 21.2–21.5 | 4.19–4.13 | m–s |
| 22.5–23.0 | 3.95–3.87 | s–vs |
| 30.2–30.5 | 2.96–2.93 | w–m |

TABLE Q

| 2θ | (AsAPO-40) d(Å) | Relative Intensity |
|---|---|---|
| 7.5–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.187 | w–m |

TABLE R

| 2θ | (AsAPO-41) d(Å) | Relative Intensity |
|---|---|---|
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.440 | w–m |

TABLE S

| 2θ | (AsAPO-42) d(Å) | Relative Intensity |
|---|---|---|
| 7.15–7.4 | 12.36–11.95 | m–vs |
| 12.5–12.7 | 7.08–6.97 | m–s |
| 21.75–21.9 | 4.09–4.06 | m–s |
| 24.1–24.25 | 3.69–3.67 | vs |
| 27.25–27.4 | 3.273–3.255 | s |
| 30.05–30.25 | 2.974–2.955 | m–s |

TABLE T

| 2θ | (AsAPO-44) d(Å) | Relative Intensity |
|---|---|---|
| 9.4–9.55 | 9.41–9.26 | vs |
| 13.0–13.1 | 6.81–6.76 | w–m |
| 16.0–16.2 | 5.54–5.47 | w–m |

TABLE T-continued

| 2θ | (AsAPO-44) d(Å) | Relative Intensity |
|---|---|---|
| 20.6–20.85 | 4.31–4.26 | s–vs |
| 24.3–24.4 | 3.66–3.65 | w–vs |
| 30.7–30.95 | 2.912–2.889 | w–s |

TABLE U

| 2θ | (AsAPO-46) d(Å) | Relative Intensity |
|---|---|---|
| 7.2–8.1 | 12.3–10.9 | vs |
| 21.2–21.8 | 4.19–4.08 | w–m |
| 22.5–23.0 | 3.95–3.87 | vw–m |
| 26.6–27.2 | 3.351–3.278 | vw–w |
| 28.5–29.0 | 3.132–3.079 | vw–w |

TABLE V

| 2θ | (AsAPO-47) d(Å) | Relative Intensity |
|---|---|---|
| 9.4 | 9.41 | vs |
| 15.9–16.0 | 5.57–5.54 | w–m |
| 20.5–20.6 | 4.33–4.31 | s |
| 24.5–24.7 | 3.63–3.60 | w |
| 25.8–25.9 | 3.45–3.44 | w |
| 30.4–30.5 | 2.940–2.931 | w |

The following examples are provided to further illustrate the invention and are not intended to be limiting thereof:

EXAMPLE (Preparation of AsAPO-5)

(a) AsAPO-5 is prepared from a reaction mixture having a composition, expressed in terms of the molar oxide ratios of the components of the reaction mixture, of:

1.0–2.0 TPA : 0.05–0.2 $As_2O_q$: 0.5–1.0 $Al_2O_3$: 0.5–1.0 $P_2O_5$ : 40–100 $H_2O$ where "TPA" denotes tripropylamine and "q" denotes the oxidation state of arsenic.

The reaction mixture is digested by placing the reaction mixture in a sealed stainless steel pressure vessel and heating it at an effective temperature and for an effective time until crystals of the AsAPO-5 product are obtained. Solids are then recovered by filtration, washed with water and dried in air at room temperature.

The AsAPO-5 product's chemical analysis shows the AsAPO-5 product contains arsenic, aluminum and phosphorus in amounts within the hexagonal compositional area defined by points A, B, C., E and F of FIG. 1.

The X-ray powder diffraction pattern of an AsAPO-5 product is characterized by the following data:

| 2θ | d(Å) | Relative Intensity |
|---|---|---|
| 7.3–7.65 | 12.1–11.56 | m–vs |
| 19.5–19.95 | 4.55–4.46 | m–s |
| 20.9–21.3 | 4.25–4.17 | m–vs |
| 22.2–22.6 | 4.00–3.93 | w–vs |
| 25.7–26.15 | 3.47–3.40 | w–m |

(b) The X-ray powder diffraction pattern for a calcined AsAPO-5 is also characterized by the X-ray pattern of part (a).

(c) When the calcined AsAPO-5 of part (b) is utilized in adsorption capacity studies using a standard McBain-Bakr gravimetric adsorption apparatus the measurements are made on a sample after activation at 350° C. in a vacuum. The following data are used in the adsorption studies:

| Adsorbate | Kinetic Diameter (Å) | Pressure (Torr) | Temp, °C. | Wt. % Adsorbed* |
|---|---|---|---|---|
| $O_2$ | 3.46 | 100 | −183 | 7 |
| $O_2$ | 3.46 | 750 | −183 | 10 |
| Neopentane | 6.2 | 700 | 24 | 4 |
| $H_2O$ | 2.65 | 4.3 | 24 | 4 |
| $H_2O$ | 2.65 | 20.0 | 24 | 12 |

*typical amount adsorbed

The pore diameter of AsAPO-5 is greater than 6.2 Å.

EXAMPLE (Preparation of AsAPO-11)

(a) A solution was formed by dissolving 11.5 grams of arsenic(V) oxide ($As_2O_5$) in 37.9 grams of water with heating. The solution was cooled and combined with 11.5 grams of 85 wt. percent orthophosphoric acid ($H_3PO_4$) The resultant solution was combined with 13.7 grams of hydrated aluminum oxide in the form of a pseudo-boehmite phase comprising 75.1 wt. percent of $Al_2O_3$ and 24.9 wt. percent of $H_2O$ and mixed until homogeneous. To the resultant gel were added 22.2 grams of water and 10.1 grams of di-n-propylamine ($C_6H_{15}N$), and the gel was mixed until homogeneous. The composition of the final reaction mixture thus produced, expressed in terms of the molar oxide ratios of the components of the reaction mixture, was:

1.0 ($C_6H_{15}N$):0.5 $As_2O_5$ : 1.00 $Al_2O_3$ : 0.5 $P_2O_5$ : 50 $H_2O$.

This final reaction mixture was digested by sealing it in a stainless steel pressure vessel lined with polytetrafluoroethylene and heating it in an oven at 200° C. under autogeneous pressure for 108 hours. The solid reaction product (which was determined by the analyses described below to be mainly AsAPO-11) was recovered by centrifugation, washed with water and dried in air at 100° C.

A sample of this solid reaction product was analyzed and the following chemical analysis obtained:

| Component | Weight percent |
|---|---|
| Carbon | 3.1 |
| $As_2O_5$ | 11.1 |
| $Al_2O_3$ | 40.0 |
| $P_2O_5$ | 32.5 |
| LOI* | 14.2 |

*LOI indicates loss on ignition.

The above chemical analysis corresponds to a product composition of:

0.03 ($C_6H_{15}N$):($As_{0.07}Al_{0.59}P_{0.34}$)$O_2$: 0.40 $H_2O$.

Microprobe analysis of an aggregate of crystals having the morphology expected for AsAPO-11 indicated the following relative proportions of arsenic, aluminum and phosphorus:

$$As_{0.05}Al_{0.046}P_{0.49}$$

so that the product contained arsenic, aluminum and phosphorus in amounts within the hexagonal compositional area defined by points A, B, C, D, E and F of FIG. 1.

The product was not pure, but the X-ray powder diffraction pattern of the major phase, as synthesized, was characterized by the data in the following Table BA (Hereinafter, Tables designated BA, BB etc. represent Tables containing all the peaks set forth in Table B above, and similarly for Tables DA, DB etc.):

TABLE BA

| | (AsAPO-11) | |
|---|---|---|
| 2θ | d(Å) | Relative Intensity 100 × I/I$_o$ |
| 8.2 | 10.81 | 51 |
| 9.5 | 9.29 | 86 |
| 13.3 | 6.67 | 24 |
| 15.8 | 5.63 | 53 |
| 19.0 | 4.66 | 9 |
| 20.5 | 4.33 | 68 |
| 21.1 | 4.21 | 90 |
| 22.2 | 4.00 | 59 |
| 22.6 | 3.92 | 56 |
| 22.8 | 3.90 | 62 |
| 23.3 | 3.82 | 100 |
| 24.8 | 3.59 | 14 |
| 26.4 | 3.37 | 13 (shoulder) |
| 26.7 | 3.34 | 24 |
| 28.0 | 3.190 | 5 |
| 28.4 | 3.142 | 18 |
| 28.7 | 3.109 | 21 |
| 29.2 | 3.061 | 6 |
| 29.6 | 3.021 | 6 |
| 31.6 | 2.833 | 8 |
| 33.0 | 2.718 | 22 |
| 34.3 | 2.615 | 12 |
| 36.6 | 2.457 | 8 |
| 36.9 | 2.436 | 5 |
| 37.7 | 2.385 | 12 |
| 37.9 | 2.374 | 15 |
| 38.4 | 2.344 | 6 |
| 38.8 | 2.321 | 8 |
| 39.5 | 2.283 | 5 |
| 45.1 | 2.009 | 6 |
| 48.9 | 1.867 | 7 |
| 50.8 | 1.797 | 5 |

The X-ray powder diffraction pattern of the major phase, after calcination by heating to 600° C. in air for 1.5 hours, was characterized by the data in the following Table BB:

TABLE BB

| | (AsAPO-11) | |
|---|---|---|
| 2θ | d(Å) | Relative Intensity 100 × I/I$_o$ |
| 8.0 | 11.00 | 30 |
| 9.8 | 9.03 | 87 |
| 11.7 | 7.56 | 7 |
| 12.8 | 6.93 | 34 |
| 13.6 | 6.50 | 9 |
| 16.1 | 5.52 | 100 |
| 19.5 | 4.54 | 17 |
| 19.8 | 4.47 | 35 |
| 20.3 | 4.36 | 18 |
| 20.7 | 4.28 | 16 |
| 21.8 | 4.07 | 97 |
| 22.1 | 4.02 | 47 |
| 22.4 | 3.79 | 62 |
| 23.5 | 3.78 | 71 |
| 24.0 | 3.70 | 13 |

TABLE BB-continued

| | (AsAPO-11) | |
|---|---|---|
| 2θ | d(Å) | Relative Intensity 100 × I/I$_o$ |
| 24.3 | 3.66 | 11 |
| 25.3 | 3.51 | 6 (shoulder) |
| 25.7 | 3.46 | 25 |
| 26.7 | 3.34 | 11 |
| 27.1 | 3.292 | 7 |
| 27.3 | 3.273 | 11 |
| 27.7 | 3.224 | 22 |
| 29.7 | 3.010 | 28 |
| 30.4 | 2.940 | 19 |
| 31.8 | 2.818 | 8 |
| 32.6 | 2.747 | 30 |
| 34.0 | 2.638 | 6 |
| 35.5 | 2.530 | 18 |
| 37.2 | 2.418 | 10 |
| 38.1 | 2.362 | 6 |
| 38.7 | 2.326 | 10 |
| 40.9 | 2.206 | 5 |
| 45.2 | 2.007 | 6 |
| 45.5 | 1.995 | 6 |
| 45.9 | 1.979 | 5 |
| 49.1 | 1.857 | 5 |
| 49.3 | 1.848 | 7 |
| 49.5 | 1.838 | 8 |
| 53.5 | 1.713 | 6 |

(b) A sample of the calcined product produced in part (a) was utilized in adsorption capacity studies using a standard McBain-Bakr gravimetric adsorption apparatus. Before being used in the adsorption tests, the sample was activated by heating to 350° C. for 16 hours in vacuum. The following data were generated in the adsorption studies:

| Adsorbate | Kinetic Diameter (Å) | Pressure (Torr) | Temp, °C. | Wt. % Adsorbed |
|---|---|---|---|---|
| $O_2$ | 3.46 | 100 | −183 | 5.8 |
| $O_2$ | 3.46 | 700 | −183 | 8.9 |
| Cyclohexane | 6.0 | 50 | 22.8 | 5.1 |

Other specimens of AsAPO-11 prepared in a similar manner had X-ray powder diffraction patterns similar to those given in Tables BA and BB above. The following general Table BC summarizes all the X-ray powder diffraction lines which were obtained from the various specimens of AsAPO-11; not all of the lines were obtained from every specimen.

TABLE BC

| | (AsAPO-11) | |
|---|---|---|
| 2θ | d(Å) | Relative Intensity 100 × I/I$_o$ |
| 8.1–8.2 | 10.81–10.91 | 33–51 |
| 9.5 | 9.29 | 58–86 |
| 13.2–13.3 | 6.67–6.71 | 14–24 |
| 15.7–15.8 | 5.63–5.65 | 34–53 |
| 19.0 | 4.66 | 5–9 |
| 20.4–20.5 | 4.33–4.35 | 35–68 |
| 20.9–21.1 | 4.21–4.25 | 90–100 |
| 22.1–22.2 | 4.00–4.02 | 57–59 |
| 22.5–22.6 | 3.92–3.95 | 54–56 |
| 22.7–22.8 | 3.90–3.92 | 34–62 |
| 23.2–23.3 | 3.82–3.84 | 62–100 |
| 24.7–24.8 | 3.59–3.60 | 10–14 |
| 26.2–26.4 | 3.37–3.40 | 13 (shoulder) |
| 26.6–26.7 | 3.34–3.35 | 15–24 |
| 28.0–28.3 | 3.190–3.155 | 5 |
| 28.4 | 3.142 | 18 |
| 28.6–28.7 | 3.109–3.116 | 13–21 |
| 29.0–29.2 | 3.061–3.076 | 5–6 |
| 29.4–29.6 | 3.021–3.037 | 6 |
| 31.4–31.6 | 2.833–2.845 | 8 |

TABLE BC-continued
(AsAPO-11)

| 2θ | d(Å) | Relative Intensity 100 × I/I₀ |
|---|---|---|
| 32.9–33.0 | 2.718–2.726 | 14–22 |
| 34.2–34.3 | 2.615–2.622 | 8–12 |
| 36.5–36.6 | 2.457–2.463 | 5–8 |
| 36.9 | 2.436 | 5 |
| 37.7 | 2.385 | 12–15 |
| 37.9 | 2.374 | 15 |
| 38.4 | 2.344 | 6 |
| 38.8 | 2.321 | 8 |
| 39.3–39.5 | 2.283–2.294 | 5 |
| 45.1 | 2.009 | 6 |
| 48.7–48.9 | 1.867–1.870 | 3–7 |
| 50.7–50.8 | 1.797–1.801 | 4–5 |

EXAMPLE 3
(Preparation of AsAPO-17)

(a) AsAPO-17 is prepared from a reaction mixture having a composition, expressed in terms of the molar oxide ratios of the components of the reaction mixture, of:

1.0–2.0 QN : 0.05–0.2 As$_2$O$_q$ : 0.5–1.0 Al$_2$O$_3$ : 0.5–1.0 P$_2$O$_5$ : 40–100 H$_2$O where "QN" denotes quinuclidine and "q" denotes the oxidation state of arsenic.

The reaction mixture is digested by placing the reaction mixture in a sealed stainless steel pressure vessel and heating it at an effective temperature and for an effective time until crystals of the AsAPO-17 product are obtained. Solids are then recovered by filtration, washed with water and dried in air at room temperature.

The AsAPO-17 product's chemical analysis shows the AsAPO-17 product contains arsenic, aluminum and phosphorus in amounts within the hexagonal compositional area defined by points A, B, C., E and F of FIG. 1.

The X-ray powder diffraction pattern of a AsAPO-17 product is characterized by the following data:

| 2θ | d(Å) | Relative Intensity |
|---|---|---|
| 7.7–7.75 | 11.5–11.4 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

(b) The X-ray powder diffraction pattern for a calcined AsAPO-17 is also characterized by the X-ray pattern of part (a).

(c) When the calcined AsAPO-17 of part (b) is utilized in adsorption capacity studies using a standard McBain-Bakr gravimetric adsorption apparatus the measurements are made on a sample after activation at 350° C. in a vacuum. The following data are used in the adsorption studies:

| Adsorbate | Kinetic Diameter (Å) | Pressure (Torr) | Temp, °C. | Wt. % Adsorbed* |
|---|---|---|---|---|
| O$_2$ | 3.46 | 100 | −183 | 10 |
| O$_2$ | 3.46 | 750 | −183 | 12 |
| n-Butane | 4.3 | 100 | 24 | 4 |
| H$_2$O | 2.65 | 4.3 | 24 | 13 |
| H$_2$O | 2.65 | 20 | 24 | 14 |

*typical amount adsorbed

The pore diameter of AsAPO-17 is about 4.3 Å.

EXAMPLE 4
(Preparation of AsAPO-31)

(a) AsAPO-31 is prepared from a reaction mixture having a composition, expressed in terms of the molar oxide ratios of the components of the reaction mixture, of:

1.0–2.0 DPA : 0.05–0.2 As$_2$O$_q$ : 0.5–1.0 Al$_2$O$_3$ 0.5–1.0 P$_2$O$_5$ : 40–100 H$_2$O where "TPA" denotes di-n-propylamine and "q" denotes the oxidation state of arsenic.

The reaction mixture is seeded with crystals of AlPO$_4$-31 (U.S. Pat. No. 4,310,440) and digested by placing the reaction mixture in a sealed stainless steel pressure vessel and heating it at an effective temperature and for an effective time until crystals of the AsAPO-31 product are obtained. Solids are then recovered by filtration, washed with water and dried in air at room temperature.

The AsAPO-31 product's chemical analysis shows the AsAPO-31 product contains arsenic, aluminum and phosphorus in amounts within the hexagonal compositional area defined by points A, B, C., E and F of FIG. 1.

The X-ray powder diffraction pattern of a AsAPO-31 product is characterized by the following data:

| 2θ | d(Å) | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

(b) The X-ray powder diffraction pattern for a calcined AsAPO-31 is also characterized by the X-ray pattern of part (a).

(c) When the calcined AsAPO-31 of part (b) is utilized in adsorption capacity studies using a standard McBain-Bakr gravimetric adsorption apparatus the measurements are made on a sample after activation at 350° C. in a vacuum. The following data are used in the adsorption studies:

| Adsorbate | Kinetic Diameter(Å) | Pressure (Torr) | Temp, °C. | Wt. % Adsorbed* |
|---|---|---|---|---|
| O$_2$ | 3.46 | 100 | −183 | 4 |
| O$_2$ | 3.46 | 750 | −183 | 6 |
| Cyclohexane | 6.0 | 90 | 24 | 3 |
| Neopentane | 6.2 | 700 | 24 | 3 |
| H$_2$O | 2.65 | 4.3 | 24 | 3 |
| H$_2$O | 2.65 | 20 | 24 | 10 |

*typical amount adsorbed

The pore diameter of AsAPO-31 is greater than about 6.2 Å.

EXAMPLE 5

(Preparation of AsAPO-34)

(a) AsAPO-34 is prepared from a reaction mixture having a composition, expressed in terms of the molar oxide ratios of the components of the reaction mixture, of:

1.0–2.0 TEAOH : 0.05–0.2 $As_2O_q$ : 0.5–1.0 $Al_2O_3$ : 0.5–1.0 $P_2O_5$ : 40–100 $H_2O$ wherein "TEAOH" denotes tetraethylammonium hydroxide and "q" denotes the oxidation state of arsenic.

The reaction mixture is digested by placing the reaction mixture in a sealed stainless steel pressure vessel and heating it at an effective temperature and for an effective time until crystals of the AsAPO-34 product are obtained. Solids are then recovered by filtration, washed with water and dried in air at room temperature.

The AsAPO-34 product's chemical analysis shows the AsAPO-34 product contains arsenic, aluminum and phosphorus in amounts within the hexagonal compositional area defined by points A, B, C., E and F of FIG. 1.

The X-ray powder diffraction pattern of a AsAPO-34 product is characterized by the following data:

| $2\theta$ | d(Å) | Relative Intensity |
|---|---|---|
| 9.4–9.65 | 9.41–9.17 | s–vs |
| 15.9–16.2 | 5.57–5.47 | vw–m |
| 17.85–18.4 | 4.97–4.82 | w–s |
| 20.3–20.9 | 4.37–4.25 | m–vs |
| 24.95–25.4 | 3.57–3.51 | vw–s |
| 30.3–30.8 | 2.95–2.90 | w–s |

(b) The X-ray powder diffraction pattern for a calcined AsAPO-34 is also characterized by the X-ray pattern of part (a).

(c) When the calcined AsAPO-34 of part (b) is utilized in adsorption capacity studies using a standard McBain-Bakr gravimetric adsorption apparatus the measurements are made on a sample after activation at 350° C. in a vacuum. The following data are used in the adsorption studies:

| Adsorbate | Kinetic Diameter(Å) | Pressure (Torr) | Temp, °C. | Wt. % Adsorbed* |
|---|---|---|---|---|
| $O_2$ | 3.46 | 100 | −183 | 13 |
| $O_2$ | 3.46 | 750 | −183 | 18 |
| n-Hexane | 4.3 | 100 | 24 | 6 |
| $H_2O$ | 2.65 | 4.3 | 24 | 15 |
| $H_2O$ | 2.65 | 20 | 24 | 21 |

*typical amount adsorbed

The pore diameter of AsAPO-34 is about 4.3 Å.

EXAMPLE 6

(Preparation of AsAPO-44)

(b) AsAPO-44 is prepared from a reaction mixture having a composition, expressed in terms of the molar oxide ratios of the components of the reaction mixture, of:

1.0–2.0 CHA : 0.0–0.2 $As_2O_q$ : 0.5–1.0 $Al_2O_3$ : 0.5–1.0 $P_2O_5$ : 40–100 $H_2O$ where "CHA" denotes cyclohexylamine and "q" denotes the oxidation state of arsenic.

The reaction mixture is digested by placing the reaction mixture in a sealed stainless steel pressure vessel and heating it at an effective temperature and for an effective time until crystals of the AsAPO-44 product are obtained. Solids are then recovered by filtration, washed with water and dried in air at room temperature.

The AsAPO-44 product's chemical analysis shows the AsAPO-44 product contains arsenic, aluminum and phosphorus in amounts within the hexagonal compositional area defined by points A, B, C., E and F of FIG. 1.

The X-ray powder diffraction pattern of a AsAPO-44 product is characterized by the following data:

| $2\theta$ | d(Å) | Relative Intensity |
|---|---|---|
| 9.4–9.55 | 9.41–9.26 | vs |
| 13.0–13.1 | 6.81–6.76 | w–m |
| 16.0–16.2 | 5.54–5.47 | w–m |
| 20.6–20.85 | 4.31–4.26 | s–vs |
| 24.3–24.4 | 3.66–3.65 | w–vs |
| 30.7–30.95 | 2.912–2.889 | w–s |

(b) The X-ray powder diffraction pattern for a calcined AsAPO-44 is also characterized by the X-ray pattern of part (a).

(c) When the calcined AsAPO-44 of part (b) is utilized in adsorption capacity studies using a standard McBain-Bakr gravimetric adsorption apparatus the measurements are made on a sample after activation at 350° C. in a vacuum. The following data are used in the adsorption studies:

| Adsorbate | Kinetic Diameter(Å) | Pressure (Torr) | Temp, °C. | Wt. % Adsorbed* |
|---|---|---|---|---|
| $O_2$ | 3.46 | 100 | −183 | 13 |
| $O_2$ | 3.46 | 750 | −183 | 16 |
| n-Hexane | 4.3 | 100 | 24 | 2 |
| $H_2O$ | 2.65 | 4.3 | 24 | 15 |
| $H_2O$ | 2.65 | 20 | 24 | 17 |

*typical amount adsorbed

The pore diameter of AsAPO-44 is about 4.3 Å.

EXAMPLE 7

(Preparation of AsAPO-16)

(a) A solution was formed by dissolving 11.5 grams of arsenic(V) oxide ($As_2O_5$) in 60.1 grams of water with heating. The solution was cooled and then combined with 11.5 grams of 85 wt. percent orthophosphoric acid ($H_3PO_4$) The resultant solution was combined with 13.7 grams of hydrated aluminum oxide in the form of a pseudo-boehmite phase comprising 75.1 wt. percent of $Al_2O_3$ and 24.9 wt. percent of $H_2O$ and mixed until homogeneous. To the resultant gel were added 11.1 grams of quinuclidine (QN), and the gel was mixed until homogeneous. The composition f the final reaction mixture thus produced, expressed in terms of the molar oxide ratios of the components of the reaction mixture, was:

1.0 QN : 0.5 $As_2O_5$ : 1.00 $Al_2O_3$ : 0.5 $P_2O_5$ : 50 $H_2O$.

This final reaction mixture was digested by sealing it in a stainless steel pressure vessel lined with polytetrafluoroethylene and heating it in an oven at 200° C. under autogeneous pressure for 23 hours. The solid reaction product (which was determined by the analyses described below to be mainly AsAPO-16) was recovered by centrifugation, washed with water and dried in air at 100° C.

A sample of this solid reaction product was analyzed and the following chemical analysis obtained:

| Component | Weight percent |
|---|---|
| Carbon | 7.3 |
| $As_2O_5$ | 7.8 |
| $Al_2O_3$ | 37.3 |
| $P_2O_5$ | 34.5 |
| LOI* | 20.7 |

*LOI indicates loss on ignition.

The above chemical analysis corresponds to a product composition of:

0.07 QN : $(As_{0.05}Al_{0.57}P_{0.38})O_2$ : 0.47 $H_2O$ .

Microprobe analysis of a clean crystal having the morphology expected for AsAPO-16 indicated the following relative proportions of arsenic, aluminum and phosphorus:

$As_{0.08}Al_{0.48}P_{0.44}$ so that the product contained arsenic, aluminum and phosphorus in amounts within the hexagonal compositional area defined by points A, B, C, D, E and F of FIG. 1.

The product was not pure, but the X-ray powder diffraction pattern of the major phase, as synthesized, was characterized by the data in the following Table DA:

TABLE DA

| (AsAPO-16) | | |
|---|---|---|
| 2θ | d(Å) | Relative Intensity 100 × $I/I_o$ |
| 11.4 | 7.76 | 75 |
| 18.7 | 4.74 | 50 |
| 22.0 | 4.05 | 100 |
| 23.0 | 3.87 | 17 |
| 26.6 | 3.353 | 27 |
| 29.0 | 3.077 | 10 |
| 29.8 | 3.000 | 26 |
| 32.7 | 2.733 | 7 |
| 34.7 | 2.578 | 6 |
| 38.0 | 2.369 | 11 |
| 39.8 | 2.263 | 3 |
| 44.4 | 2.041 | 3 |
| 48.5 | 1.876 | 7 |
| 52.4 | 1.745 | 2 |
| 54.8 | 1.674 | 2 |

The X-ray powder diffraction pattern of the major phase, after calcination by heating at 600° C. in air for 2.5 hours, was characterized by the data in the following Table DB:

TABLE DB

| (AsAPO-16) | | |
|---|---|---|
| 2θ | d(Å) | Relative Intensity 100 × $I/I_o$ |
| 11.4 | 7.73 | 100 |
| 18.7 | 4.74 | 22 |
| 22.0 | 4.04 | 53 |
| 23.0 | 3.87 | 13 |
| 26.6 | 3.351 | 21 |

TABLE DB-continued

| (AsAPO-16) | | |
|---|---|---|
| 2θ | d(Å) | Relative Intensity 100 × $I/I_o$ |
| 29.0 | 3.076 | 11 |
| 29.8 | 2.997 | 29 |
| 32.8 | 2.734 | 5 |
| 34.7 | 2.587 | 5 |
| 34.8 | 2.578 | 6 |
| 38.0 | 2.370 | 5 |
| 39.8 | 2.267 | 3 |
| 44.2 | 2.050 | 2 |
| 48.5 | 1.878 | 4 |
| 52.5 | 1.742 | 2 |

(b) A sample of the calcined product produced in part (a) was utilized in adsorption capacity studies using a standard McBain-Bakr gravimetric adsorption apparatus. Before being used in the adsorption tests, the sample was activated by heating to 350° C. for 16 hours in vacuum. The following data were generated in the adsorption studies:

| Adsorbate | Kinetic Diameter (Å) | Pressure (Torr) | Temp, °C. | Wt. % Adsorbed |
|---|---|---|---|---|
| $O_2$ | 3.46 | 101 | −183 | 1.0 |
| $O_2$ | 3.46 | 708 | −183 | 3.8 |
| $H_2O$ | 2.65 | 20.0 | 22.8 | 29.6 |
| $H_2O$ | 2.65 | 4.6 | 22.8 | 17.6 |

From the above data, the pore size of the calcined product was determined to be greater than 2.6 Å, as shown by the adsorption of water (kinetic diameter of 2.65 Å) and less than 3.5 Å, as shown by the negligible adsorption of oxygen (kinetic diameter of 3.46 Å).

Other specimens of AsAPO-16 prepared in a similar manner had X-ray powder diffraction patterns similar to those given in Tables DA and DB above. The following general Table DC summarizes all the X-ray powder diffraction lines which were obtained from the various specimens of AsAPO-16; not all of the lines were obtained from every specimen.

TABLE DC

| (AsAPO-16) | | |
|---|---|---|
| 2θ | d(Å) | Relative Intensity 100 × $I/I_o$ |
| 11.4–11.5 | 7.70–7.76 | 63–75 |
| 18.7–18.8 | 4.73–4.74 | 50–51 |
| 22.0 | 4.05 | 100 |
| 23.0 | 3.87 | 16–17 |
| 26.6 | 3.353 | 26–27 |
| 29.0–29.1 | 3.071–3.077 | 10–11 |
| 29.8 | 3.000 | 26–28 |
| 32.7–32.8 | 2.733 | 5–7 |
| 34.7–34.8 | 2.577–2.578 | 6–7 |
| 38.0 | 2.369 | 11 |
| 39.8 | 2.263 | 3 |
| 44.4 | 2.041 | 3 |
| 48.5 | 1.876 | 7 |
| 52.4 | 1.745 | 2–3 |

EXAMPLE 8

(Preparation of AsAPO-18)

(a) A solution was formed by dissolving 17.2 grams of arsenic(V) oxide ($As_2O_5$) in 57.3 grams of water with heating. The solution was cooled and combined with 5.8 grams of 85 wt. percent orthophosphoric acid ($H_3PO_4$) and 36.8 grams of 40 percent aqueous tetraethylammonium hydroxide (Et$_4$NOH). The resultant solution was combined with 40.9 grams of aluminum isopropoxide and mixed until homogeneous. The composition of the final reaction mixture thus produced, expressed in terms of the molar oxide ratios of the components of the reaction mixture, was:

Et$_4$NOH : 0.75 As$_2$O$_5$ : 1.00 Al$_2$O$_3$ : 0.25 P$_2$O$_5$ : 45 H$_2$O 6.0 i-C$_3$H$_7$OH.

This final reaction mixture was digested by sealing it in a stainless steel pressure vessel lined with polytetrafluoroethylene and heating it in an oven at 200° C. under autogeneous pressure for 65 hours. The solid reaction product (which was determined by the analyses described below to be mainly AsAPO-18) was recovered by centrifugation, washed with water and dried in air at 100° C.

Microprobe analysis of a clean crystal having the morphology expected for AsAPO-18 indicated the following relative proportions of arsenic, aluminum and phosphorus:

As$_{0.30}$Al$_{0.41}$P$_{0.29}$ so that the product contained arsenic, aluminum and phosphorus in amounts within the hexagonal compositional area defined by points A, B, C, D, E and F of FIG. 1.

The product was not pure, but the X-ray powder diffraction pattern of the major phase, as synthesized, was characterized by the data in the following Table FA:

TABLE FA

| (AsAPO-18) | | |
|---|---|---|
| 2θ | d(Å) | Relative Intensity 100 × I/I$_o$ |
| 9.5 | 9.27 | 100 |
| 10.3 | 8.61 | 5 |
| 10.9 | 8.15 | 9 |
| 13.0 | 6.82 | 6 |
| 13.9 | 6.37 | 7 |
| 14.7 | 6.02 | 7 |
| 15.4 | 5.76 | 8 |
| 16.9 | 5.26 | 24 |
| 17.7 | 5.01 | 9 |
| 20.0 | 4.44 | 22 |
| 20.8 | 4.27 | 25 |
| 22.0 | 4.04 | 9 |
| 22.6 | 3.94 | 5 |
| 24.2 | 3.68 | 8 |
| 24.7 | 3.600 | 6 |
| 25.9 | 3.445 | 10 |
| 26.5 | 3.363 | 8 |
| 27.8 | 3.205 | 7 |
| 29.7 | 3.006 | 8 |
| 30.5 | 2.933 | 8 |
| 31.0 | 2.883 | 10 |
| 32.1 | 2.791 | 12 |

EXAMPLE 9

(Preparation of AsAPO-18)

(a) A reaction mixture was formed by dissolving 11.5 grams of arsenic(V) oxide (As$_2$O$_5$) and 11.5 grams of 85 wt. percent orthophosphoric acid (H$_3$PO$_4$) in 48.1 grams of water and then combining the resultant solution with 36.8 grams of 40 percent aqueous tetraethylammonium hydroxide (Et$_4$NOH). The resultant mixture was combined with 30.6 grams of aluminum isopropoxide and mixed until homogeneous. The composition of the final reaction mixture thus produced, expressed in terms of the molar oxide ratios of the components of the reaction mixture, was:

1.0 Et$_4$NOH : 0.5 As$_2$O$_5$ : 0.75 Al$_2$O$_3$ : 0.5 P$_2$O$_5$ : 40 H$_2$O 4.5 i-C$_3$H$_7$OH.

This final reaction mixture was digested by sealing it in a stainless steel pressure vessel lined with polytetrafluoroethylene and heating it in an oven at 200° C. under autogeneous pressure for 16 hours. The solid reaction product (which was determined by the analyses described below to be mainly AsAPO-18) was recovered by centrifugation, washed with water and dried in air at 100° C.

A sample of this solid reaction product was analyzed and the following chemical analysis obtained:

| Component | Weight percent |
|---|---|
| Carbon | 7.0 |
| As$_2$O$_5$ | 14.2 |
| Al$_2$O$_3$ | 33.2 |
| P$_2$O$_5$ | 34.8 |
| H$_2$O | 12.1 |

The above chemical analysis corresponds to a product composition of:

0.06 Et$_4$NOH : (As$_{0.1}$ Al$_{0.51}$P$_{0.39}$)O$_2$ : 0.53 H$_2$O.

Microprobe analysis of a relatively clean crystal having the morphology expected for AsAPO-18 indicated the following relative proportions of arsenic, aluminum and phosphorus:

As$_{0.11}$Al$_{0.50}$P$_{0.39}$ so that the product contained arsenic, aluminum and phosphorus in amounts within the hexagonal compositional area defined by points A, B, C, D, E and F of FIG. 1.

The product was not pure, but the X-ray powder diffraction pattern of the major phase, as synthesized, was characterized by the data in the following Table FB:

TABLE FB

| (AsAPO-18) | | |
|---|---|---|
| 2θ | d(Å) | Relative Intensity 100 × I/I$_o$ |
| 9.6 | 9.19 | 100 |
| 10.5 | 8.45 | 5 |
| 11.0 | 8.01 | 7 |
| 13.2 | 6.73 | 4 |
| 14.0 | 6.32 | 6 |
| 14.8 | 5.98 | 5 |
| 15.5 | 5.70 | 18 |
| 17.0 | 5.21 | 43 |
| 17.9 | 4.95 | 10 |
| 19.3 | 4.61 | 3 |
| 19.5 | 4.55 | 4 |
| 20.2 | 4.40 | 19 |
| 21.0 | 4.14 | 40 |
| 22.1 | 4.03 | 13 |
| 23.8 | 3.73 | 2 |
| 24.4 | 3.65 | 8 |
| 24.9 | 3.57 | 5 |
| 25.1 | 3.543 | 3 |
| 26.1 | 3.417 | 8 |
| 26.4 | 3.378 | 6 |
| 26.8 | 3.329 | 7 |
| 28.0 | 3.184 | 7 |
| 29.0 | 3.075 | 2 |
| 30.0 | 2.979 | 13 |

TABLE FB-continued (AsAPO-18)

| 2θ | d(Å) | Relative Intensity 100 × I/I$_o$ |
|---|---|---|
| 30.7 | 2.909 | 9 |
| 31.3 | 2.860 | 10 |
| 31.8 | 2.816 | 4 |
| 32.4 | 2.765 | 14 |
| 33.4 | 2.682 | 3 |
| 34.3 | 2.612 | 2 |
| 36.1 | 2.487 | 3 |
| 42.8 | 2.113 | 4 |
| 44.2 | 2.050 | 2 |
| 49.5 | 1.842 | 4 |
| 50.9 | 1.795 | 3 |
| 54.3 | 1.690 | 2 |

The X-ray powder diffraction pattern of the major phase, after calcination by heating to 400° C. in a vacuum, was characterized by the data in the following Table FC:

TABLE FC (AsAPO-18)

| 2θ | d(Å) | Relative Intensity 100 × I/I$_o$ |
|---|---|---|
| 9.7 | 9.16 | 100 |
| 10.8 | 8.20 | 13 |
| 13.0 | 6.80 | 14 |
| 13.5 | 6.54 | 7 |
| 16.4 | 5.41 | 6 |
| 17.2 | 5.17 | 16 |
| 20.8 | 4.28 | 9 |
| 21.6 | 4.11 | 12 |
| 23.2 | 3.83 | 5 |
| 24.0 | 3.71 | 12 |
| 26.0 | 3.432 | 5 |
| 26.5 | 3.365 | 7 |
| 28.3 | 3.159 | 7 |
| 31.2 | 2.866 | 13 |
| 33.1 | 2.709 | 4 |

(b) A sample of the calcined product produced in part (a) was utilized in adsorption capacity studies using a standard McBain-Bakr gravimetric adsorption apparatus. Before being used in the adsorption tests, the sample was activated by heating to 350° C. for 16 hours in vacuum. The following data were generated in the adsorption studies:

| Adsorbate | Kinetic Diameter (Å) | Pressure (Torr) | Temp, °C. | Wt. % Adsorbed |
|---|---|---|---|---|
| O$_2$ | 3.46 | 103 | −183 | 18.3 |
| O$_2$ | 3.46 | 750 | −183 | 24.2 |
| n-Hexane | 4.3 | 45 | 21.5 | 9.3 |
| iso-Butane | 5.0 | 101 | 21.3 | 0.4 |
| H$_2$O | 2.65 | 4.6 | 21.4 | 25.9 |
| H$_2$O | 2.65 | 18.0 | 21.6 | 34.8 |

From the above data, the pore size of the calcined product was determined to be greater than 4.3 Å, as shown by the adsorption of n-hexane (kinetic diameter of 4.3 Å) and less than 5.0 Å, as shown by the negligible adsorption of iso-butane (kinetic diameter of 5.0 Å).

Other specimens of AsAPO-18 prepared in a similar manner had X-ray powder diffraction patterns similar to those given in Tables FA, FB and F above. The following general Table FD summarizes all the X-ray powder diffraction lines which were obtained from the various specimens of AsAPO-18; not all of the lines were obtained from every specimen.

TABLE FD (AsAPO-18)

| 2θ | d(Å) | Relative Intensity 100 × I/I$_o$ |
|---|---|---|
| 9.5–9.6 | 9.19–9.27 | 100 |
| 10.3–10.5 | 8.45–8.61 | 5 |
| 10.9–11.0 | 8.01–8.15 | 7–9 |
| 13.0–13.2 | 6.73–6.82 | 4–6 |
| 13.9–14.0 | 6.32–6.37 | 7 |
| 14.7–14.8 | 5.98–6.02 | 5–7 |
| 15.4–15.5 | 5.70–5.76 | 8–18 |
| 16.9–17.0 | 5.21–5.26 | 24–43 |
| 17.7–17.9 | 4.95–5.01 | 9–10 |
| 20.0–20.2 | 4.40–4.44 | 19–22 |
| 20.8–21.0 | 4.24–4.27 | 25–40 |
| 22.0–22.1 | 4.02–4.04 | 9–13 |
| 22.6 | 3.94 | 5 |
| 24.2–24.4 | 3.65–3.68 | 8 |
| 24.7–24.9 | 3.573–3.600 | 5–6 |
| 25.9 | 3.445 | 10 |
| 26.5–26.8 | 3.329–3.363 | 7–8 |
| 27.8–28.0 | 3.184–3.203 | 7 |
| 29.7–30.0 | 2.979–3.006 | 8–13 |
| 30.5–30.7 | 2.909–2.933 | 8–9 |
| 31.0–31.3 | 2.860–2.883 | 10 |
| 32.1–32.4 | 2.765–2.791 | 12–14 |

PROCESS APPLICATIONS

The AsAPO compositions of the present invention are, in general, hydrophilic and adsorb water preferentially over common hydrocarbon molecules such as paraffins, olefins and aromatic species, e.g., benzene, xylenes and cumene. Thus the present molecular sieve compositions as a class are useful as desiccants in such adsorption separation/purification processes as natural gas drying, cracked gas drying. Water is also preferentially adsorbed over the so-called permanent gases such as carbon dioxide, nitrogen, oxygen and hydrogen. These AsAPOs are therefore suitably employed in the drying of reformer hydrogen streams and in the drying of oxygen, nitrogen or air prior to liquifaction.

The present AsAPO compositions also exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art (e.g. ion exchange or impregnation) and used, for example, in fabricating catalyst compositions having silica or alumina bases. Of the general class, those species having pores larger than about 4 Å are preferred for catalytic applications.

Among the hydrocarbon conversion reactions catalyzed by AsAPO compositions are cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization.

Using AsAPO catalyst compositions which contain a hydrogenation promoter such as platinum or palladium, heavy petroleum residual stocks, cyclic stocks and other hydrocrackable charge stocks, can be hydrocracked at temperatures in the range of 400° F. to 825° F. (204° C. to 441° C.) using molar ratios of hydrogen to hydrocarbon in the range of between 2 and 80, pressures between 10 and 3500 p.s.i.g. (0.171 to 24.23 MPa.), and a liquid hourly space velocity (LHSV) of from 0.1 to 20, preferably 1.0 to 10.

The AsAPO catalyst compositions employed in hydrocracking are also suitable for use in reforming processes in which the hydrocarbon feedstocks contact the catalyst at temperatures of from about 700° F. to 1000° F. (371° C. to 538° C.), hydrogen pressures of from 100 to 500 p.s.i.g. (0.791 to 3.448 MPa.), LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerization processes in which feedstocks such as normal paraffins are converted to saturated branched chain isomers. Hydroisomerization is carried out at a temperature of from about 200° F. to 600° F. (93° C. to 316° C.), preferably 300° F. to 550° F. (149° C. to 288° C.) with an LHSV value of from about 0.2 to 1.0. Hydrogen (H) is supplied to the reactor in admixture with the hydrocarbon (Hc) feedstock in molar proportions (H/Hc) of between 1 and 5.

At somewhat higher temperatures, i.e. from about 650° F. to 1000° F. (343° C. to 538° C.), preferably 850° F. to 950° F. (454° C. to 510° C.) and usually at somewhat lower pressures within the range of about 15 to 50 p.s.i.g. (205 to 446 KPa.), the same catalyst compositions are used to hydroisomerize normal paraffins. Preferably the paraffin feedstock comprises normal paraffins having a carbon number range of $C_7$–$C_{20}$. Contact time between the feedstock and the catalyst is generally relatively short to avoid undesirable side reactions such as olefin polymerization and paraffin cracking. LHSV values in the range of 0.1 to 10, preferably 1.0 to 6.0 are suitable.

The unique crystal structure of the present AsAPO catalysts and their availability in a form totally void of alkali metal content favor their use in the conversion of alkylaromatic compounds, particularly the catalytic disproportionation of toluene, ethylene, trimethyl benzenes, tetramethyl benzenes and the like. In the disproportionation process, isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-% of the overall composition. Extraneous hydrogen can, but need not, be present in the reaction zone which is maintained at a temperature of from about 400° to 750° F. (204° to 399° C.), pressures in the range of 100 to 2000 p.s.i.g. (0.791 to 13.89 MPa.) and LHSV values in the range of 0.1 to 15.

Catalytic cracking processes are preferably carried out with AsAPO compositions using feedstocks such as gas oils, heavy naphthas, deasphalted crude oil residua, etc., with gasoline being the principal desired product. Temperature conditions of 850° to 1100° F. (454° to 593° C.), LHSV values of 0.5 to 10 and pressure conditions of from about 0 to 50 p.s.i.g. (101 to 446 KPa.) are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the AsAPO catalyst in conjunction with a Group VIII non-noble metal cation such as cobalt and nickel.

I catalytic dealkylation wherein it is desired to cleave paraffinic side chains from aromatic nuclei without substantially hydrogenating the ring structure, relatively high temperatures in the range of about 800°–1000° F. (427°–538° C.) are employed at moderate hydrogen pressures of about 300–1000 p.s.i.g. (2.17 6.895 MPa.), other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like. Any of these may contain up to about 5 weight-percent of sulfur and up to about 3 weigh-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of hydrocracking catalysts. Consequently, it is necessary to operate at more extreme conditions when it is desired to obtain the same degree of hydrocracking conversion per pass on a relatively nitrogenous feed than with a feed containing less organonitrogen compounds. Consequently, the conditions under which denitrogenation, desulfurization and/or hydrocracking can be most expeditiously accomplished in any given situation are necessarily determined in view of the characteristics of the feedstocks, in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g., organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°–900° F. (260°–482° C.), while paraffins, naphthenes and alkyl aromatics are isomerized at temperatures of 700°–1000° F. (371°–538° C.). Particularly desirable isomerization reactions contemplated herein include the conversion of n-heptene and/or n-octane to isoheptanes, iso-octanes, butane to iso-butane, methylcyclopentane to cyclohexane, meta-xylene and/or ortho-xylene to paraxylene, 1-butene to 2-butene and/or isobutene, n-hexane to isohexene, cyclohexene to methylcyclopentene etc. The preferred form of the catalyst is a combination of the AsAPO with polyvalent metal compounds (such as sulfides) of metals of Group II-A, Group II-B and rare earth metals. For alkylation and dealkylation processes the AsAPO compositions having pores of at least 5Å are preferred. When employed for dealkylation of alkyl aromatics, the temperature is usually at least 350° F. (177° C.) and ranges up to a temperature at which substantial cracking of the feedstock or conversion products occurs, generally up to about 700° F. (371° C.). The temperature is preferably at least 450° F. (232° C.) and not greater than the critical temperature of the compound undergoing dealkylation. Pressure conditions are applied to retain at least the aromatic feed in the liquid state. For alkylation the temperature can be as low as 250° F. (121° C.) but is preferably at least 350° F. (177° C.). In the alkylation of benzene, toluene and xylene, the preferred alkylating agents are olefins such as ethylene and propylene.

We claim:

1. Crystalline molecular sieves having three-dimensional microporous framework structures of $AsO_2$, $AlO_2$ and $PO_2$ tetrahedral units having an empirical chemical composition on an anhydrous basis expressed by the formula:

$$mR : (As_xAl_yP_z)O_2$$

wherein "R" represents at least one organic templating agent present in the intracrystalline pore system; "m" represents the molar amount of "R" present per mole of $(As_xAl_yP_z)O_2$ and has a value of from zero to about 0.3; and "x", "y" and "z" represent the mole fractions of arsenic, aluminum and phosphorus, respectively, present as tetrahedral oxides, said mole fractions being such that they are within the hexagonal compositional area defined by points A, B, C, D, E and F of FIG. 1, said crystalline molecular sieves having a characteristic X-ray powder diffraction pattern which contains at least the d-spacings set forth in one of the following Tables J, K, O, Q, R, S. and V:

TABLE J*

| 2θ | d(Å) | Relative Intensity |
|---|---|---|
| (AsAPO-33) | | |
| 9.25–9.55 | 9.56–9.26 | w–m |
| 12.5–12.9 | 7.08–6.86 | vs |
| 16.9–17.3 | 5.25–5.13 | w–m |
| 20.45–20.9 | 4.34–4.25 | w–m |
| 23.85–24.25 | 3.73–3.67 | w–m |
| 26.05–26.35 | 3.42–3.38 | w–m |
| 27.3–27.6 | 3.27–3.23 | vs |

*as-synthesized form

TABLE K*

| 2θ | d(Å) | Relative Intensity |
|---|---|---|
| (AsAPO-33) | | |
| 13.15–13.4 | 6.73–6.61 | vs |
| 18.05–18.35 | 4.91–4.83 | m |
| 18.4–18.6 | 4.82–4.77 | m |
| 26.55–26.7 | 3.36–3.34 | m |
| 32.0–32.1 | 2.80–2.79 | m |

*calcined form

TABLE O

| 2θ | d(Å) | Relative Intensity |
|---|---|---|
| (AsAPO-37) | | |
| 6.1–6.3 | 14.49–14.03 | vs |

TABLE O-continued

| 2θ | d(Å) | Relative Intensity |
|---|---|---|
| (AsAPO-37) | | |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

TABLE Q

| 2θ | d(Å) | Relative Intensity |
|---|---|---|
| (AsAPO-40) | | |
| 7.6–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.187 | w–m |

TABLE R

| 2θ | d(Å) | Relative Intensity |
|---|---|---|
| (AsAPO-41) | | |
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.440 | w–m |

TABLE S

| 2θ | d(Å) | Relative Intensity |
|---|---|---|
| (AsAPO-42) | | |
| 7.15–7.4 | 12.36–11.95 | m–vs |
| 12.5–12.7 | 7.08–6.97 | m–s |
| 21.75–21.9 | 4.09–4.06 | m–s |
| 24.1–24.25 | 3.69–3.67 | vs |
| 27.25–27.4 | 3.273–3.255 | s |
| 30.05–30.25 | 2.974–2.955 | m–s |

TABLE U

| 2θ | d(Å) | Relative Intensity |
|---|---|---|
| (AsAPO-46) | | |
| 7.2–8.1 | 12.3–10.9 | vs |
| 21.2–21.8 | 4.19–4.08 | w–m |
| 22.5–23.0 | 3.95–3.87 | vw–m |
| 26.6–27.2 | 3.351–3.278 | vw–w |
| 28.5–29.0 | 3.132–3.079 | vw–w |

2. Crystalline molecular sieves according to claim 1 wherein the mole fraction of arsenic, aluminum and phosphorus present as tetrahedral oxides are within the tetragonal compositional area defined by points a, b, c, and d of FIG. 2.

3. Crystalline molecular sieves according to claim 1 wherein the mole fractions of arsenic, aluminum and phosphorus present as tetrahedral oxides are within the tetragonal compositional area defined by points e, f, g and h of FIG. 3.

4. The crystalline molecular sieves according to claim 3 wherein the mole fractions of arsenic, aluminum and phosphorus present as tetrahedral oxides are within the hexagonal compositional area defined by points i, j, k, l, m and n of FIG. 3.

5. The crystalline molecular sieves according to claim 1 wherein "m" is not greater than about 0.15.

6. The crystalline molecular sieves of claim 1 having a characteristic X-ray powder diffraction pattern which contains at least the d-spacings set forth in Table J given in claim 1.

7. The crystalline molecular sieves of claim 1 having a characteristic X-ray powder diffraction pattern which contains at least the d-spacings set forth in Table K given in claim 1.

8. The crystalline molecular sieves of claim 1 having a characteristic X-ray powder diffraction pattern which contains at least the d-spacings set forth in Table O given in claim 1.

9. The crystalline molecular sieves of claim 1 having a characteristic X-ray powder diffraction pattern which contains at least the d-spacings set forth in Table Q given in claim 1.

10. The crystalline molecular sieves of claim 1 having a characteristic X-ray powder diffraction pattern which contains at least the d-spacings set forth in Table R given in claim 1.

11. The crystalline molecular sieves of claim 1 having a characteristic X-ray powder diffraction pattern which contains at least the d-spacings set forth in Table S given in claim 1.

12. The crystalline molecular sieves of claim 1 having a characteristic X-ray powder diffraction pattern which contains at least the d-spacings set forth in Table U given in claim 1.

13. Molecular sieves prepared by calcining, at a temperature sufficiently high to remove at least some of any organic templating agent present in the intracrystalline pore system, crystalline molecular sieves having three-dimensional microporous framework structures of $AsO_2$, $AlO_2$ and $PO_2$ tetrahedral units having an empirical chemical composition on a an anhydrous basis expressed by the formula:

$$mR : (As_xAl_yP_z)O_2$$

wherein "R" represents at least one organic templating agent present in the intracrystalline pore system; "m" represents the molar amount of "R" present per mole of $(As_xAl_yP_z)O_2$ and has a value of from zero to about 0.3; and "x", "y" and "z"]represent the mole fractions of arsenic, aluminum and phosphorus, respectively, present as tetrahedral oxides, said mole fractions being such that they are within the hexagonal compositional area defined by points A, B, C, D, E and F of FIG. 1, said crystalline molecular sieves having a characteristic X-ray powder diffraction pattern which contains at least the d-spacings set forth in one of the following Tables J, K, O, Q, R, S, and V:

TABLE J*

| 2θ | (AsAPO-33) d(Å) | Relative Intensity |
|---|---|---|
| 9.25–9.55 | 9.56–9.26 | w–m |
| 12.5–12.9 | 7.08–6.86 | vs |
| 16.9–17.3 | 5.25–5.13 | w–m |
| 20.45–20.9 | 4.34–4.25 | w–m |
| 23.85–24.25 | 3.73–3.67 | w–m |
| 26.05–26.35 | 3.42–3.38 | w–m |

TABLE J*-continued

| 2θ | (AsAPO-33) d(Å) | Relative Intensity |
|---|---|---|
| 27.3–27.6 | 3.27–3.23 | vs |

*as-synthesized form

TABLE K*

| 2θ | (AsAPO-33) d(Å) | Relative Intensity |
|---|---|---|
| 13.15–13.4 | 6.73–6.61 | vs |
| 18.05–18.35 | 4.91–4.83 | m |
| 18.4–18.6 | 4.82–4.77 | m |
| 26.55–26.7 | 3.36–3.34 | m |
| 32.0–32.1 | 2.80–2.79 | m |

*calcined form

TABLE O

| 2θ | (AsAPO-37) d(Å) | Relative Intensity |
|---|---|---|
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

TABLE Q

| 2θ | (AsAPO-40) d(Å) | Relative Intensity |
|---|---|---|
| 7.6–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.187 | w–m |

TABLE R

| 2θ | (AsAPO-41) d(Å) | Relative Intensity |
|---|---|---|
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.440 | w–m |

TABLE S

| 2θ | (AsAPO-42) d(Å) | Relative Intensity |
|---|---|---|
| 7.15–7.4 | 12.36–11.95 | m–vs |
| 12.5–12.7 | 7.08–6.97 | m–s |
| 21.75–21.9 | 4.09–4.06 | m–s |
| 24.1–24.25 | 3.69–3.67 | vs |
| 27.25–27.4 | 3.273–3.255 | s |
| 30.05–30.25 | 2.974–2.955 | m–s |

TABLE U

| 2θ | (AsAPO-46) d(Å) | Relative Intensity |
|---|---|---|
| 7.2–8.1 | 12.3–10.9 | vs |
| 21.2–21.8 | 4.19–4.08 | w–m |
| 22.5–23.0 | 3.95–3.87 | vw–m |
| 26.6–27.2 | 3.351–3.278 | vw–w |
| 28.5–29.0 | 3.132–3.079 | vw–w |

* * * * *